(12) United States Patent
Conway et al.

(10) Patent No.: US 11,607,524 B2
(45) Date of Patent: *Mar. 21, 2023

(54) CATHETER GRIP AND METHOD

(71) Applicant: Rochester Medical Corporation, Stewartville, MN (US)

(72) Inventors: Anthony J. Conway, Chatfield, MN (US); Patrick H. McLeod, Pulborough (GB); Sarah L. Grinde, Spring Grove, MN (US); Jeremy M. Wiste, Stewartville, MN (US)

(73) Assignee: Rochester Medical Corporation, Stewartville, MN (US)

( * ) Notice: Subject to any disclaimer, the term of this patent is extended or adjusted under 35 U.S.C. 154(b) by 404 days.

This patent is subject to a terminal disclaimer.

(21) Appl. No.: 16/790,404

(22) Filed: Feb. 13, 2020

(65) Prior Publication Data
US 2020/0179647 A1    Jun. 11, 2020

Related U.S. Application Data

(63) Continuation of application No. 15/649,296, filed on Jul. 13, 2017, now Pat. No. 10,569,051, which is a
(Continued)

(51) Int. Cl.
*A61M 25/00* (2006.01)
*A61M 25/01* (2006.01)

(52) U.S. Cl.
CPC .... *A61M 25/0097* (2013.01); *A61M 25/0017* (2013.01); *A61M 25/0111* (2013.01)

(58) Field of Classification Search
CPC ............ A61M 25/0017; A61M 25/002; A61M 25/0111; A61M 25/0009; A61M 25/00;
(Continued)

(56) References Cited

U.S. PATENT DOCUMENTS

| 480,911 A | 8/1892 | Vance |
| 822,092 A | 5/1906 | Woodruff |

(Continued)

FOREIGN PATENT DOCUMENTS

| CA | 763930 A | 7/1967 |
| CN | 2139835 Y | 8/1993 |

(Continued)

OTHER PUBLICATIONS

U.S. Appl. No. 13/705,695, filed Dec. 5, 2012 Final Office Action dated Apr. 23, 2015.
(Continued)

*Primary Examiner* — Adam Marcetich
(74) *Attorney, Agent, or Firm* — Rutan & Tucker LLP

(57) ABSTRACT

A method for introducing a urinary catheter of a urinary catheter package, the urinary catheter package including a grip designed for sliding movement over the urinary catheter. The grip can include a body designed to surround the urinary catheter shaft, a first flare, and a second flare. The body can include a proximal end, a distal end, and a gripping area between the proximal end and the distal end, the gripping area designed to contact the urinary catheter upon the application of force to the gripping area. The first flare can increase in cross-sectional area from the gripping area to the proximal end of the body. The second flare can increase in cross-sectional area from the gripping area to the distal end of the body. The method includes removing the urinary catheter from a proximal end of the urinary catheter package.

14 Claims, 4 Drawing Sheets

Related U.S. Application Data continuation of application No. 13/047,175, filed on Mar. 14, 2011, now Pat. No. 9,707,375.

(58) Field of Classification Search
CPC .............. A61M 25/01; A61M 25/0113; A61M 25/013; A61M 2210/1089; A61M 2210/1078; A61M 2039/087; A61M 2202/0496; A61F 5/453
See application file for complete search history.

(56) References Cited

U.S. PATENT DOCUMENTS

| | | |
|---|---|---|
| 1,235,142 A | 7/1917 | Ichilian |
| 1,643,289 A | 9/1927 | Peglay |
| 1,661,494 A | 3/1928 | Nielsen |
| 2,043,630 A | 6/1936 | Raiche |
| 2,213,210 A | 9/1940 | Egbert |
| 2,228,992 A | 1/1941 | Fry |
| 2,230,226 A | 2/1941 | Auzin |
| 2,248,934 A | 7/1941 | Auzin |
| 2,285,502 A | 6/1942 | Dreyfus |
| 2,308,484 A | 1/1943 | Auzin et al. |
| 2,314,262 A | 3/1943 | Winder |
| 2,320,157 A | 5/1943 | Raiche |
| 2,322,858 A | 6/1943 | Limbert et al. |
| 2,330,399 A | 9/1943 | Winder |
| 2,330,400 A | 9/1943 | Winder |
| 2,389,831 A | 11/1945 | Welsh |
| 2,390,070 A | 12/1945 | Auzin |
| 2,481,488 A | 9/1949 | Auzin |
| 2,494,393 A | 1/1950 | Lamson |
| 2,610,626 A | 9/1952 | Edwards |
| 2,638,093 A | 5/1953 | Kulick |
| 2,649,619 A | 8/1953 | Killian |
| 2,649,854 A | 8/1953 | Salm |
| 2,690,595 A | 10/1954 | Raiche |
| 2,712,161 A | 7/1955 | Moss |
| 2,856,932 A | 10/1958 | Griffitts |
| 2,912,981 A | 11/1959 | Keough |
| 3,044,468 A | 7/1962 | Birtwell |
| 3,053,257 A | 9/1962 | Birtwell |
| 3,076,464 A | 2/1963 | Rosenberg |
| 3,154,080 A | 10/1964 | Rowan et al. |
| 3,169,527 A | 2/1965 | Sheridan |
| 3,211,151 A | 10/1965 | Foderick et al. |
| 3,304,353 A | 2/1967 | Harautuneian |
| 3,345,988 A | 10/1967 | Vitello |
| 3,394,704 A | 7/1968 | Dery |
| 3,394,705 A | 7/1968 | Abramson |
| 3,403,682 A | 10/1968 | McDonell |
| 3,409,016 A | 11/1968 | Foley |
| 3,434,869 A | 3/1969 | Davidson |
| 3,463,141 A | 8/1969 | Mozolf |
| 3,503,400 A | 3/1970 | Osthagen |
| 3,508,959 A | 4/1970 | Krahnke |
| 3,509,884 A | 5/1970 | Bell |
| 3,520,305 A | 7/1970 | Davis |
| 3,539,674 A | 11/1970 | Dereniuk et al. |
| 3,544,668 A | 12/1970 | Dereniuk |
| 3,548,805 A | 12/1970 | Datsenko |
| 3,556,294 A | 1/1971 | Walck et al. |
| 3,566,874 A | 3/1971 | Shepherd et al. |
| 3,593,713 A | 7/1971 | Bogoff et al. |
| 3,598,127 A | 8/1971 | Wepsic |
| 3,606,889 A | 9/1971 | Arblaster |
| 3,642,004 A | 2/1972 | Osthagen et al. |
| 3,646,929 A | 3/1972 | Bonnar |
| 3,648,704 A | 3/1972 | Jackson |
| 3,683,928 A | 8/1972 | Kuntz |
| 3,695,921 A | 10/1972 | Shepherd et al. |
| 3,699,956 A | 10/1972 | Kitrilakis et al. |
| 3,699,964 A | 10/1972 | Ericson |
| 3,708,324 A | 1/1973 | Stebleton |
| 3,726,281 A | 4/1973 | Norton et al. |
| 3,739,783 A | 6/1973 | Broerman |
| 3,762,399 A | 10/1973 | Riedell |
| 3,768,102 A | 10/1973 | Kwan-Gett et al. |
| 3,788,324 A | 1/1974 | Lim |
| 3,794,042 A | 2/1974 | De Klotz et al. |
| 3,797,478 A | 3/1974 | Walsh et al. |
| 3,838,728 A | 10/1974 | Voegele |
| 3,841,304 A | 10/1974 | Jones |
| 3,853,130 A * | 12/1974 | Sheridan ............ A61M 25/0111 128/DIG. 26 |
| 3,854,483 A | 12/1974 | Powers |
| 3,861,395 A | 1/1975 | Taniguchi |
| 3,875,937 A | 4/1975 | Schmitt et al. |
| 3,879,516 A | 4/1975 | Wolvek |
| 3,882,220 A | 5/1975 | Ryder |
| 3,889,685 A | 6/1975 | Miller, Jr. et al. |
| 3,894,540 A | 7/1975 | Bonner, Jr. |
| 3,898,993 A | 8/1975 | Taniguchi |
| 3,903,893 A | 9/1975 | Scheer |
| 3,924,634 A | 12/1975 | Taylor et al. |
| 3,926,705 A | 12/1975 | Todd |
| 3,930,580 A | 1/1976 | Bazell et al. |
| 3,934,721 A | 1/1976 | Juster et al. |
| 3,962,519 A | 6/1976 | Rusch et al. |
| 3,967,728 A | 7/1976 | Gordon et al. |
| 3,981,299 A | 9/1976 | Murray |
| 3,983,879 A | 10/1976 | Todd |
| 4,026,296 A | 5/1977 | Stoy et al. |
| 4,029,104 A | 6/1977 | Kerber |
| 4,055,682 A | 10/1977 | Merrill |
| 4,062,363 A | 12/1977 | Bonner, Jr. |
| 4,091,922 A | 5/1978 | Egler |
| 4,119,094 A | 10/1978 | Micklus et al. |
| 4,120,715 A | 10/1978 | Ockwell et al. |
| 4,133,303 A | 1/1979 | Patel |
| 4,140,127 A | 2/1979 | Cianci et al. |
| 4,149,539 A | 4/1979 | Cianci |
| 4,168,699 A | 9/1979 | Hauser |
| 4,186,745 A | 2/1980 | Lewis et al. |
| 4,187,851 A | 2/1980 | Hauser |
| 4,196,731 A | 4/1980 | Laurin et al. |
| 4,198,983 A | 4/1980 | Becker et al. |
| 4,198,984 A | 4/1980 | Taylor |
| 4,209,010 A | 6/1980 | Ward et al. |
| 4,225,371 A | 9/1980 | Taylor et al. |
| 4,230,115 A | 10/1980 | Walz, Jr. et al. |
| 4,246,909 A | 1/1981 | Wu et al. |
| 4,249,535 A | 2/1981 | Hargest, III |
| 4,252,760 A | 2/1981 | Foster et al. |
| 4,265,848 A | 5/1981 | Rusch |
| 4,266,999 A | 5/1981 | Baier |
| 4,269,310 A | 5/1981 | Uson |
| 4,284,459 A | 8/1981 | Patel et al. |
| 4,287,227 A | 9/1981 | Kamada et al. |
| 4,311,146 A | 1/1982 | Wonder |
| 4,311,659 A | 1/1982 | Rey et al. |
| 4,318,406 A | 3/1982 | McLeod |
| 4,318,947 A | 3/1982 | Joung |
| 4,341,817 A | 7/1982 | Tozier et al. |
| 4,342,392 A | 8/1982 | Cox |
| 4,343,788 A | 8/1982 | Mustacich et al. |
| 4,366,901 A | 1/1983 | Short |
| 4,367,732 A | 1/1983 | Poulsen et al. |
| 4,378,018 A | 3/1983 | Alexander et al. |
| 4,378,796 A | 4/1983 | Milhaud |
| 4,379,506 A | 4/1983 | Davidson |
| 4,381,008 A | 4/1983 | Thomas et al. |
| 4,381,380 A | 4/1983 | LeVeen et al. |
| 4,395,806 A | 8/1983 | Wonder et al. |
| 4,411,648 A | 10/1983 | Davis et al. |
| 4,419,097 A | 12/1983 | Rowland |
| 4,428,365 A | 1/1984 | Hakky |
| 4,446,860 A | 5/1984 | Gutnick |
| 4,457,299 A | 7/1984 | Cornwell |
| 4,472,226 A | 9/1984 | Redinger et al. |
| 4,475,910 A | 10/1984 | Conway et al. |
| 4,477,325 A | 10/1984 | Osburn |
| 4,479,795 A | 10/1984 | Mustacich et al. |
| 4,515,593 A | 5/1985 | Norton |
| 4,534,768 A | 8/1985 | Osburn et al. |

(56) References Cited

U.S. PATENT DOCUMENTS

| | | |
|---|---|---|
| 4,539,234 A | 9/1985 | Sakamoto et al. |
| 4,540,409 A | 9/1985 | Nystrom et al. |
| 4,553,533 A | 11/1985 | Leighton |
| 4,563,184 A | 1/1986 | Korol |
| 4,568,340 A | 2/1986 | Giacalone |
| 4,571,239 A | 2/1986 | Heyman |
| 4,571,240 A | 2/1986 | Samson et al. |
| 4,576,599 A | 3/1986 | Lipner |
| 4,581,026 A | 4/1986 | Schneider |
| 4,581,028 A | 4/1986 | Fox, Jr. et al. |
| 4,582,762 A | 4/1986 | Onohara et al. |
| 4,586,974 A | 5/1986 | Nystrom et al. |
| 4,589,874 A | 5/1986 | Riedel et al. |
| 4,592,920 A | 6/1986 | Murtfeldt |
| 4,597,765 A | 7/1986 | Klatt |
| 4,597,931 A | 7/1986 | Watanabe et al. |
| 4,601,713 A | 7/1986 | Fuqua |
| 4,603,152 A | 7/1986 | Laurin et al. |
| 4,612,337 A | 9/1986 | Fox, Jr. et al. |
| 4,613,324 A | 9/1986 | Ghajar |
| 4,615,692 A | 10/1986 | Giacalone et al. |
| 4,615,697 A | 10/1986 | Robinson |
| 4,622,033 A | 11/1986 | Taniguchi |
| 4,623,329 A | 11/1986 | Drobish et al. |
| 4,626,250 A | 12/1986 | Schneider |
| 4,627,844 A | 12/1986 | Schmitt |
| 4,633,863 A | 1/1987 | Filips et al. |
| 4,634,433 A | 1/1987 | Osborne |
| 4,637,907 A | 1/1987 | Hegel et al. |
| 4,638,790 A | 1/1987 | Conway et al. |
| 4,640,668 A | 2/1987 | Yang |
| 4,640,688 A | 2/1987 | Hauser |
| 4,652,259 A | 3/1987 | O'Neil |
| 4,664,657 A | 5/1987 | Williamitis et al. |
| 4,673,401 A | 6/1987 | Jensen et al. |
| 4,677,143 A | 6/1987 | Laurin et al. |
| 4,685,913 A | 8/1987 | Austin |
| 4,686,124 A | 8/1987 | Onohara et al. |
| 4,687,470 A | 8/1987 | Okada |
| 4,692,152 A | 9/1987 | Emde |
| 4,699,616 A | 10/1987 | Nowak et al. |
| 4,710,169 A | 12/1987 | Christopher |
| 4,710,181 A | 12/1987 | Fuqua |
| 4,713,067 A | 12/1987 | Rothenberg et al. |
| 4,731,064 A | 3/1988 | Heyden |
| 4,737,219 A | 4/1988 | Taller et al. |
| 4,739,768 A | 4/1988 | Engelson |
| 4,747,845 A | 5/1988 | Korol |
| 4,754,877 A | 7/1988 | Johansson et al. |
| 4,759,753 A | 7/1988 | Schneider et al. |
| 4,768,503 A | 9/1988 | Highgate et al. |
| 4,769,013 A | 9/1988 | Lorenz et al. |
| 4,769,099 A | 9/1988 | Therriault et al. |
| 4,772,473 A | 9/1988 | Patel et al. |
| 4,773,901 A | 9/1988 | Norton |
| 4,775,371 A | 10/1988 | Mueller, Jr. |
| 4,790,834 A | 12/1988 | Austin |
| 4,790,835 A | 12/1988 | Elias |
| D299,865 S | 2/1989 | Kamstrup-Larsen et al. |
| 4,810,247 A | 3/1989 | Glassman |
| 4,811,847 A | 3/1989 | Reif et al. |
| 4,813,935 A | 3/1989 | Haber et al. |
| 4,820,270 A | 4/1989 | Hardcastle et al. |
| 4,820,289 A | 4/1989 | Coury et al. |
| 4,820,291 A | 4/1989 | Terauchi et al. |
| 4,820,292 A | 4/1989 | Korol et al. |
| 4,834,721 A | 5/1989 | Onohara et al. |
| 4,838,876 A | 6/1989 | Wong et al. |
| 4,846,784 A | 7/1989 | Haber |
| 4,846,909 A | 7/1989 | Klug et al. |
| 4,850,969 A | 7/1989 | Jackson |
| 4,861,337 A | 8/1989 | George |
| 4,863,424 A | 9/1989 | Blake, III et al. |
| 4,863,444 A | 9/1989 | Blomer |
| 4,863,449 A | 9/1989 | Therriault et al. |
| 4,867,748 A | 9/1989 | Samuelsen |
| 4,874,373 A | 10/1989 | Luther et al. |
| 4,876,109 A | 10/1989 | Mayer et al. |
| 4,885,049 A | 12/1989 | Johannesson |
| 4,894,059 A | 1/1990 | Larsen et al. |
| 4,902,503 A | 2/1990 | Umemura et al. |
| 4,904,260 A | 2/1990 | Ray et al. |
| 4,917,113 A | 4/1990 | Conway et al. |
| 4,917,686 A | 4/1990 | Bayston et al. |
| 4,919,966 A | 4/1990 | Shlenker |
| RE33,206 E | 5/1990 | Conway et al. |
| 4,923,450 A | 5/1990 | Maeda et al. |
| 4,925,668 A | 5/1990 | Khan et al. |
| 4,930,522 A | 6/1990 | Busnel et al. |
| 4,931,056 A | 6/1990 | Ghajar et al. |
| 4,932,938 A | 6/1990 | Goldberg et al. |
| 4,932,948 A | 6/1990 | Kernes et al. |
| 4,934,999 A | 6/1990 | Bader |
| 4,935,260 A | 6/1990 | Shlenker |
| 4,950,256 A | 8/1990 | Luther et al. |
| 4,952,618 A | 8/1990 | Olsen |
| 4,963,137 A | 10/1990 | Heyden |
| 4,968,294 A | 11/1990 | Salama |
| 4,968,507 A | 11/1990 | Zentner et al. |
| 4,976,703 A | 12/1990 | Franetzki et al. |
| 4,981,471 A | 1/1991 | Quinn et al. |
| 4,994,047 A | 2/1991 | Walker et al. |
| 5,004,454 A | 4/1991 | Beyar et al. |
| 5,007,897 A | 4/1991 | Kalb et al. |
| 5,013,306 A | 5/1991 | Solomon et al. |
| 5,013,717 A | 5/1991 | Solomon et al. |
| 5,019,096 A | 5/1991 | Fox, Jr. et al. |
| 5,019,378 A | 5/1991 | Allen |
| 5,019,601 A | 5/1991 | Allen |
| 5,059,190 A | 10/1991 | Novak |
| 5,071,406 A | 12/1991 | Jang |
| 5,078,707 A | 1/1992 | Peter Klug |
| 5,082,006 A | 1/1992 | Jonasson |
| 5,084,037 A | 1/1992 | Barnett |
| 5,087,252 A | 2/1992 | Denard |
| 5,088,980 A | 2/1992 | Leighton |
| 5,089,205 A | 2/1992 | Huang et al. |
| 5,090,424 A | 2/1992 | Simon et al. |
| 5,098,379 A | 3/1992 | Conway et al. |
| 5,102,401 A | 4/1992 | Lambert et al. |
| 5,102,405 A | 4/1992 | Conway et al. |
| 5,109,378 A | 4/1992 | Proctor et al. |
| 5,109,601 A | 5/1992 | McBride |
| 5,112,306 A | 5/1992 | Burton et al. |
| 5,114,398 A | 5/1992 | Trick et al. |
| 5,128,088 A | 7/1992 | Shimomura et al. |
| 5,131,906 A | 7/1992 | Chen |
| 5,137,671 A | 8/1992 | Conway et al. |
| 5,140,999 A | 8/1992 | Ardito |
| 5,147,341 A | 9/1992 | Starke et al. |
| 5,165,952 A | 11/1992 | Solomon et al. |
| 5,176,666 A | 1/1993 | Conway et al. |
| 5,197,957 A | 3/1993 | Wendler |
| 5,201,713 A | 4/1993 | Rossetti |
| 5,201,724 A | 4/1993 | Hukins et al. |
| 5,209,726 A | 5/1993 | Goosen |
| 5,211,640 A | 5/1993 | Wendler |
| 5,226,530 A | 7/1993 | Golden |
| 5,234,411 A | 8/1993 | Vaillancourt et al. |
| 5,236,422 A | 8/1993 | Eplett, Jr. |
| 5,242,391 A | 9/1993 | Place et al. |
| 5,242,428 A | 9/1993 | Palestrant |
| 5,261,896 A | 11/1993 | Conway et al. |
| 5,263,947 A | 11/1993 | Kay |
| 5,269,755 A | 12/1993 | Bodicky |
| 5,269,770 A | 12/1993 | Conway et al. |
| 5,270,358 A | 12/1993 | Asmus |
| 5,279,600 A | 1/1994 | Hogan |
| 5,290,306 A | 3/1994 | Trotta et al. |
| 5,300,052 A | 4/1994 | Kubo |
| 5,306,226 A | 4/1994 | Salama |
| 5,312,383 A | 5/1994 | Kubalak |
| 5,334,175 A | 8/1994 | Conway et al. |
| 5,335,775 A | 8/1994 | Scanlon et al. |

(56) References Cited

U.S. PATENT DOCUMENTS

| | | |
|---|---|---|
| 5,336,211 A | 8/1994 | Metz |
| 5,346,483 A | 9/1994 | Thaxton, Sr. |
| 5,348,536 A | 9/1994 | Young et al. |
| 5,352,182 A | 10/1994 | Kalb et al. |
| 5,360,402 A | 11/1994 | Conway et al. |
| 5,366,449 A | 11/1994 | Gilberg |
| 5,368,575 A | 11/1994 | Chang |
| 5,370,899 A | 12/1994 | Conway et al. |
| 5,376,085 A | 12/1994 | Conway et al. |
| 5,380,312 A | 1/1995 | Goulter |
| 5,395,333 A | 3/1995 | Brill |
| 5,402,886 A | 4/1995 | McGlinch |
| 5,409,495 A | 4/1995 | Osborn |
| 5,415,635 A | 5/1995 | Bagaoisan et al. |
| 5,417,226 A | 5/1995 | Juma |
| 5,417,666 A | 5/1995 | Coulter |
| 5,423,784 A | 6/1995 | Metz |
| 5,433,705 A | 7/1995 | Giebel et al. |
| 5,433,713 A | 7/1995 | Trotta |
| 5,447,231 A | 9/1995 | Kastenhofer |
| 5,451,424 A | 9/1995 | Solomon et al. |
| 5,454,798 A | 10/1995 | Kubalak et al. |
| 5,464,650 A | 11/1995 | Berg et al. |
| 5,479,945 A | 1/1996 | Simon |
| 5,482,740 A | 1/1996 | Conway et al. |
| 5,483,976 A | 1/1996 | McLaughlin et al. |
| 5,501,669 A | 3/1996 | Conway et al. |
| 5,509,427 A | 4/1996 | Simon et al. |
| 5,513,659 A | 5/1996 | Buuck et al. |
| 5,513,660 A | 5/1996 | Simon et al. |
| 5,531,715 A | 7/1996 | Engelson et al. |
| 5,531,717 A | 7/1996 | Roberto et al. |
| 5,538,584 A | 7/1996 | Metz |
| 5,549,924 A | 8/1996 | Shlenker et al. |
| 5,554,141 A | 9/1996 | Wendler |
| 5,562,599 A | 10/1996 | Beyschlag |
| 5,567,495 A | 10/1996 | Modak et al. |
| 5,569,219 A | 10/1996 | Hakki et al. |
| 5,582,599 A | 12/1996 | Daneshvar |
| 5,593,718 A | 1/1997 | Conway et al. |
| 5,599,321 A | 2/1997 | Conway et al. |
| 5,614,143 A | 3/1997 | Hager |
| 5,622,711 A | 4/1997 | Chen |
| 5,624,395 A | 4/1997 | Mikhail et al. |
| 5,630,429 A | 5/1997 | Dann |
| 5,633,010 A | 5/1997 | Chen |
| 5,634,475 A | 6/1997 | Wolvek |
| 5,643,235 A | 7/1997 | Figuerido |
| 5,670,111 A | 9/1997 | Conway et al. |
| 5,670,557 A | 9/1997 | Dietz et al. |
| 5,671,755 A | 9/1997 | Simon et al. |
| 5,674,561 A | 10/1997 | Dietz et al. |
| 5,679,399 A | 10/1997 | Shlenker et al. |
| 5,695,485 A | 12/1997 | Duperret et al. |
| 5,702,381 A | 12/1997 | Cottenden |
| 5,707,357 A | 1/1998 | Mikhail et al. |
| 5,709,672 A | 1/1998 | Illner |
| 5,711,841 A | 1/1998 | Jaker |
| 5,724,994 A | 3/1998 | Simon et al. |
| 5,730,733 A | 3/1998 | Mortier et al. |
| 5,736,152 A | 4/1998 | Dunn |
| 5,752,525 A | 5/1998 | Simon et al. |
| 5,752,944 A | 5/1998 | Dann et al. |
| 5,756,144 A | 5/1998 | Wolff et al. |
| 5,762,996 A | 6/1998 | Lucas et al. |
| 5,779,632 A | 7/1998 | Dietz et al. |
| 5,779,670 A | 7/1998 | Bidwell et al. |
| 5,795,332 A | 8/1998 | Lucas et al. |
| 5,795,334 A | 8/1998 | Cochrane, III |
| 5,795,524 A | 8/1998 | Basso, Jr. et al. |
| 5,806,527 A | 9/1998 | Borodulin et al. |
| 5,810,789 A | 9/1998 | Powers et al. |
| 5,820,607 A | 10/1998 | Tcholakian et al. |
| 5,827,247 A | 10/1998 | Kay |
| 5,827,249 A | 10/1998 | Jensen |
| 5,830,932 A | 11/1998 | Kay |
| 5,853,518 A | 12/1998 | Utas |
| 5,853,750 A | 12/1998 | Dietz et al. |
| 5,865,821 A | 2/1999 | Lowey |
| 5,877,243 A | 3/1999 | Sarangapani |
| 5,895,374 A * | 4/1999 | Rødsten .............. A61M 25/002 |
| | | 206/364 |
| 5,897,535 A | 4/1999 | Feliziani et al. |
| 5,902,631 A | 5/1999 | Wang et al. |
| 5,906,575 A | 5/1999 | Conway et al. |
| 5,931,303 A | 8/1999 | Salvadori |
| 5,931,304 A | 8/1999 | Hammond |
| 5,971,954 A | 10/1999 | Conway et al. |
| 5,980,483 A | 11/1999 | Dimitri |
| 5,980,507 A | 11/1999 | Fassuliotis et al. |
| 6,004,305 A | 12/1999 | Hursman et al. |
| 6,007,524 A | 12/1999 | Schneider |
| 6,007,526 A | 12/1999 | Passalaqua et al. |
| 6,042,562 A | 3/2000 | Amor |
| 6,050,934 A | 4/2000 | Mikhail et al. |
| 6,053,905 A | 4/2000 | Daignault, Jr. et al. |
| 6,059,107 A | 5/2000 | Nøsted et al. |
| 6,063,063 A | 5/2000 | Harboe et al. |
| 6,065,597 A | 5/2000 | Pettersson et al. |
| 6,068,618 A | 5/2000 | Anderson |
| 6,090,075 A | 7/2000 | House |
| 6,098,625 A | 8/2000 | Winkler |
| 6,102,929 A | 8/2000 | Conway et al. |
| 6,113,582 A | 9/2000 | Dwork |
| 6,119,697 A | 9/2000 | Engel et al. |
| 6,131,575 A | 10/2000 | Lenker et al. |
| 6,132,399 A | 10/2000 | Shultz |
| 6,186,990 B1 | 2/2001 | Chen et al. |
| 6,206,885 B1 | 3/2001 | Ghahremani et al. |
| 6,231,501 B1 | 5/2001 | Ditter |
| 6,254,570 B1 | 7/2001 | Rutner et al. |
| 6,261,255 B1 | 7/2001 | Mullis et al. |
| 6,261,271 B1 | 7/2001 | Solomon et al. |
| 6,280,425 B1 | 8/2001 | Del Guercio |
| 6,296,627 B1 | 10/2001 | Edwards |
| 6,299,598 B1 | 10/2001 | Bander |
| 6,299,602 B1 * | 10/2001 | Miller .............. A61M 25/0631 |
| | | 604/165.01 |
| 6,315,711 B1 | 11/2001 | Conway et al. |
| 6,326,421 B1 | 12/2001 | Lipman |
| 6,355,004 B1 | 3/2002 | Pedersen et al. |
| 6,379,334 B1 | 4/2002 | Frassica |
| 6,383,434 B2 | 5/2002 | Conway et al. |
| 6,387,080 B1 | 5/2002 | Rødsten |
| 6,391,010 B1 | 5/2002 | Wilcox |
| 6,402,726 B1 | 6/2002 | Genese |
| 6,409,717 B1 | 6/2002 | Israelsson et al. |
| 6,436,085 B1 | 8/2002 | Lauer |
| 6,437,038 B1 | 8/2002 | Chen |
| 6,440,060 B1 | 8/2002 | Latour, Jr. |
| 6,468,245 B2 | 10/2002 | Alexandersen |
| 6,471,268 B1 | 10/2002 | Stenstrom et al. |
| 6,479,000 B2 | 11/2002 | Conway et al. |
| 6,479,726 B1 | 11/2002 | Cole |
| 6,509,319 B1 | 1/2003 | Raad et al. |
| 6,551,293 B1 | 4/2003 | Mitchell |
| 6,558,369 B2 | 5/2003 | Rosenblum |
| 6,558,792 B1 | 5/2003 | Vaabengaard et al. |
| 6,578,709 B1 | 6/2003 | Kavanagh et al. |
| 6,579,539 B2 | 6/2003 | Lawson et al. |
| 6,582,401 B1 | 6/2003 | Windheuser et al. |
| 6,596,401 B1 | 7/2003 | Terry et al. |
| 6,602,244 B2 | 8/2003 | Kavanagh et al. |
| 6,613,014 B1 | 9/2003 | Chi |
| 6,626,888 B1 | 9/2003 | Conway et al. |
| 6,632,204 B2 | 10/2003 | Guldfeldt et al. |
| 6,634,498 B2 | 10/2003 | Kayerød et al. |
| 6,638,269 B2 | 10/2003 | Wilcox |
| 6,659,937 B2 | 12/2003 | Polsky et al. |
| 6,682,555 B2 | 1/2004 | Cioanta et al. |
| 6,693,189 B2 | 2/2004 | Holt et al. |
| 6,695,831 B1 | 2/2004 | Tsukada et al. |
| 6,716,895 B1 | 4/2004 | Terry |
| 6,719,709 B2 | 4/2004 | Whalen et al. |

(56) References Cited

U.S. PATENT DOCUMENTS

| | | |
|---|---|---|
| 6,723,350 B2 | 4/2004 | Burrell et al. |
| 6,733,474 B2 | 5/2004 | Kusleika |
| 6,736,805 B2 | 5/2004 | Israelsson et al. |
| 6,740,273 B2 | 5/2004 | Lee |
| 6,767,551 B2 | 7/2004 | McGhee et al. |
| D496,266 S | 9/2004 | Nestenborg |
| 6,787,156 B1 | 9/2004 | Bar-Shalom |
| 6,797,743 B2 | 9/2004 | McDonald et al. |
| 6,803,420 B2 | 10/2004 | Cleary et al. |
| 6,848,574 B1 | 2/2005 | Israelsson et al. |
| 6,849,070 B1 | 2/2005 | Hansen et al. |
| 6,852,105 B2 | 2/2005 | Bolmsjo et al. |
| D503,335 S | 3/2005 | Risberg et al. |
| 6,869,416 B2 | 3/2005 | Windheuser et al. |
| 6,872,195 B2 | 3/2005 | Modak et al. |
| 6,887,230 B2 | 5/2005 | Kubalak et al. |
| 6,939,339 B1 | 9/2005 | Axexandersen et al. |
| 6,939,554 B2 | 9/2005 | McDonald et al. |
| 6,949,090 B1 | 9/2005 | Leers et al. |
| 6,951,902 B2 | 10/2005 | McDonald et al. |
| 7,001,370 B2 | 2/2006 | Kubalak et al. |
| 7,033,367 B2 | 4/2006 | Ghahremani et al. |
| 7,066,912 B2 | 6/2006 | Nestenborg et al. |
| 7,087,048 B2 | 8/2006 | Israelsson et al. |
| 7,094,220 B2 | 8/2006 | Tanghoj et al. |
| 7,160,277 B2 | 1/2007 | Elson et al. |
| 7,166,092 B2 | 1/2007 | Elson et al. |
| 7,204,940 B2 | 4/2007 | McDonald et al. |
| 7,211,275 B2 | 5/2007 | Ying et al. |
| 7,294,117 B2 | 11/2007 | Provost-tine et al. |
| 7,311,698 B2 | 12/2007 | Tanghoj et al. |
| 7,329,412 B2 | 2/2008 | Modak et al. |
| 7,331,948 B2 | 2/2008 | Skarda |
| 7,334,679 B2 | 2/2008 | Givens, Jr. |
| 7,374,040 B2 | 5/2008 | Lee et al. |
| 7,380,658 B2 | 6/2008 | Murray et al. |
| 7,381,768 B2 | 6/2008 | Wiercinski et al. |
| 7,402,559 B2 | 7/2008 | Catania et al. |
| 7,445,812 B2 | 11/2008 | Schmidt et al. |
| 7,458,964 B2 | 12/2008 | Mosler et al. |
| 7,476,223 B2 | 1/2009 | McBride |
| 7,507,229 B2 | 3/2009 | Hewitt et al. |
| 7,517,343 B2 | 4/2009 | Tanghoj et al. |
| 7,571,804 B2 | 8/2009 | Kjellmann Bruun et al. |
| 7,601,158 B2 | 10/2009 | House |
| 7,615,045 B2 | 11/2009 | Israelsson et al. |
| 7,628,784 B2 | 12/2009 | Diaz et al. |
| 7,632,256 B2 | 12/2009 | Mosler et al. |
| D609,819 S | 2/2010 | Tomes et al. |
| 7,662,146 B2 | 2/2010 | House |
| 7,670,331 B2 | 3/2010 | Tanghoej |
| 7,682,353 B2 | 3/2010 | Tanghoj et al. |
| 7,691,476 B2 | 4/2010 | Finley |
| 7,717,902 B2 | 5/2010 | Sauer |
| 7,749,529 B2 | 7/2010 | Ash et al. |
| 7,767,291 B2 | 8/2010 | Taylor |
| 7,770,726 B2 | 8/2010 | Murray et al. |
| 7,770,728 B2 | 8/2010 | Kærn |
| 7,780,642 B2 | 8/2010 | Rasmussen et al. |
| 7,789,873 B2 | 9/2010 | Kubalak et al. |
| 7,823,722 B2 | 11/2010 | Bezou et al. |
| 7,846,133 B2 | 12/2010 | Windheuser et al. |
| 7,867,220 B2 | 1/2011 | Tanghoj |
| 7,886,907 B2 | 2/2011 | Murray et al. |
| 7,918,831 B2 | 4/2011 | House |
| 7,938,838 B2 | 5/2011 | House |
| 7,947,021 B2 | 5/2011 | Bourne et al. |
| 7,985,217 B2 | 7/2011 | Mosler et al. |
| 8,011,505 B2 | 9/2011 | Murray et al. |
| 8,051,981 B2 | 11/2011 | Murray et al. |
| 8,052,673 B2 | 11/2011 | Nestenborg |
| 8,058,341 B2 | 11/2011 | Tosaki et al. |
| 8,066,693 B2 | 11/2011 | Tanghoj et al. |
| 8,127,922 B2 | 3/2012 | Nordholm et al. |
| 8,163,327 B2 | 4/2012 | Finley |
| 8,177,774 B2 | 5/2012 | House |
| 8,181,778 B1 | 5/2012 | van Groningen et al. |
| 8,192,413 B2 | 6/2012 | Bjerregaard |
| 8,205,745 B2 | 6/2012 | Murray et al. |
| 8,207,393 B2 | 6/2012 | Bach |
| 8,230,993 B2 | 7/2012 | Tanghoej |
| 8,267,919 B2 | 9/2012 | Utas et al. |
| 8,282,624 B2 | 10/2012 | Tanghoej et al. |
| 8,287,519 B2 | 10/2012 | Smith |
| 8,298,202 B2 | 10/2012 | McCray |
| 8,303,556 B2 | 11/2012 | White |
| 8,328,792 B2 | 12/2012 | Nishtala et al. |
| 8,356,457 B2 | 1/2013 | Murray et al. |
| 8,409,171 B2 | 4/2013 | Hannon et al. |
| 8,454,569 B2 | 6/2013 | Kull-Osterlin et al. |
| 8,459,455 B2 | 6/2013 | Frojd |
| 8,475,434 B2 | 7/2013 | Frojd |
| 8,864,730 B2 | 10/2014 | Conway et al. |
| 9,707,375 B2 | 7/2017 | Conway et al. |
| 9,872,969 B2 | 1/2018 | Conway et al. |
| 10,092,728 B2 | 10/2018 | Conway et al. |
| 10,569,051 B2 | 2/2020 | Conway et al. |
| 10,639,451 B2 | 5/2020 | Kearns et al. |
| 2001/0001443 A1 | 5/2001 | Kayerod et al. |
| 2001/0031933 A1 | 10/2001 | Cannon |
| 2001/0054562 A1 | 12/2001 | Pettersson et al. |
| 2002/0013564 A1 | 1/2002 | Kubalek et al. |
| 2002/0032406 A1 | 3/2002 | Kusleika |
| 2002/0103467 A1 | 8/2002 | Kubalak |
| 2002/0147265 A1 | 10/2002 | Ding et al. |
| 2002/0169438 A1 | 11/2002 | Sauer |
| 2002/0182265 A1 | 12/2002 | Burrell et al. |
| 2003/0004496 A1 | 1/2003 | Tanghoj |
| 2003/0018293 A1 | 1/2003 | Tanghoj et al. |
| 2003/0018302 A1 | 1/2003 | Kavanagh et al. |
| 2003/0018321 A1 | 1/2003 | Rosenblum |
| 2003/0018322 A1 | 1/2003 | Tanghoj et al. |
| 2003/0055403 A1 | 3/2003 | Nestenborg et al. |
| 2003/0060807 A1 | 3/2003 | Tanghoj et al. |
| 2003/0083644 A1* | 5/2003 | Avaltroni ............ A61L 2/20 604/328 |
| 2003/0114823 A1 | 6/2003 | Bosselaar et al. |
| 2003/0130646 A1 | 7/2003 | Kubalak et al. |
| 2003/0168365 A1 | 9/2003 | Kaem |
| 2004/0030301 A1 | 2/2004 | Hunter |
| 2004/0055925 A1 | 3/2004 | Franks-Farah et al. |
| 2004/0074794 A1 | 4/2004 | Conway et al. |
| 2004/0082926 A1 | 4/2004 | Bruns |
| 2004/0097892 A1 | 5/2004 | Evans et al. |
| 2004/0133156 A1 | 7/2004 | Diaz et al. |
| 2004/0133226 A1 | 7/2004 | Buckman et al. |
| 2004/0153049 A1 | 8/2004 | Hewitt et al. |
| 2004/0153051 A1 | 8/2004 | Israelsson et al. |
| 2004/0158231 A1 | 8/2004 | Tanghoj et al. |
| 2004/0163980 A1 | 8/2004 | Tanghoj et al. |
| 2004/0193143 A1 | 9/2004 | Sauer |
| 2004/0234572 A1 | 11/2004 | Martinod et al. |
| 2004/0236293 A1 | 11/2004 | Tanghoj et al. |
| 2004/0249343 A1 | 12/2004 | Cioanta |
| 2004/0254562 A1 | 12/2004 | Tanghoj et al. |
| 2004/0256264 A1 | 12/2004 | Israelsson et al. |
| 2005/0015076 A1 | 1/2005 | Giebmeyer et al. |
| 2005/0031872 A1 | 2/2005 | Schmidt et al. |
| 2005/0043715 A1 | 2/2005 | Nestenborg et al. |
| 2005/0049577 A1 | 3/2005 | Snell et al. |
| 2005/0070882 A1 | 3/2005 | McBride |
| 2005/0080399 A1 | 4/2005 | Bolmsjo et al. |
| 2005/0096688 A1 | 5/2005 | Slazas et al. |
| 2005/0101924 A1 | 5/2005 | Elson et al. |
| 2005/0109648 A1 | 5/2005 | Kerzman et al. |
| 2005/0137582 A1 | 6/2005 | Kull-Osterlin et al. |
| 2005/0148950 A1 | 7/2005 | Windheuser et al. |
| 2005/0177104 A1 | 8/2005 | Conway |
| 2005/0199521 A1 | 9/2005 | Givens |
| 2005/0214443 A1 | 9/2005 | Madsen |
| 2005/0282977 A1 | 12/2005 | Stempel et al. |
| 2005/0283136 A1 | 12/2005 | Skarda |
| 2006/0004332 A1 | 1/2006 | Marx |
| 2006/0025753 A1 | 2/2006 | Kubalak et al. |

(56) References Cited

U.S. PATENT DOCUMENTS

| | | |
|---|---|---|
| 2006/0041246 A1 | 2/2006 | Provost-tine et al. |
| 2006/0058777 A1 | 3/2006 | Nielsen |
| 2006/0163097 A1 | 7/2006 | Murray et al. |
| 2006/0196783 A1 | 9/2006 | Bruun et al. |
| 2006/0229576 A1 | 10/2006 | Conway et al. |
| 2006/0240069 A1 | 10/2006 | Utas et al. |
| 2007/0016168 A1 | 1/2007 | Conway |
| 2007/0026472 A1 | 2/2007 | Prokash et al. |
| 2007/0088330 A1 | 4/2007 | House |
| 2007/0149946 A1 | 6/2007 | Viswanathan et al. |
| 2007/0161971 A1 | 7/2007 | House |
| 2008/0015527 A1 | 1/2008 | House |
| 2008/0082051 A1 | 4/2008 | Miller et al. |
| 2008/0091145 A1 | 4/2008 | House |
| 2008/0103464 A1 | 5/2008 | Mosler et al. |
| 2008/0119803 A1 | 5/2008 | Lund |
| 2008/0172040 A1 | 7/2008 | Smith |
| 2008/0172042 A1 | 7/2008 | House |
| 2008/0179208 A1 | 7/2008 | Murray et al. |
| 2008/0183262 A1 | 7/2008 | Dowling |
| 2008/0215021 A1 | 9/2008 | Cisko, Jr. et al. |
| 2008/0243081 A1 | 10/2008 | Nance et al. |
| 2008/0279907 A1 | 11/2008 | Ash et al. |
| 2009/0000970 A1 | 1/2009 | Bordeau et al. |
| 2009/0005725 A1 | 1/2009 | Shorey |
| 2009/0043287 A1 | 2/2009 | Mosler et al. |
| 2009/0048570 A1 | 2/2009 | Jensen |
| 2009/0101531 A1 | 4/2009 | Nordholm et al. |
| 2009/0131917 A1 | 5/2009 | Kavanagh et al. |
| 2009/0163884 A1 | 6/2009 | Kull-Osterlin et al. |
| 2009/0200187 A1 | 8/2009 | Nestenborg et al. |
| 2009/0208368 A1* | 8/2009 | Waldrep .............. A61M 25/002 206/219 |
| 2009/0221992 A1 | 9/2009 | Hannon et al. |
| 2009/0234294 A1 | 9/2009 | Harvey et al. |
| 2009/0240214 A1 | 9/2009 | Conway et al. |
| 2009/0247827 A1 | 10/2009 | Secrest et al. |
| 2010/0010086 A1 | 1/2010 | Ash et al. |
| 2010/0025273 A1 | 2/2010 | Matsuda et al. |
| 2010/0030197 A1 | 2/2010 | House |
| 2010/0036363 A1 | 2/2010 | Watanabe et al. |
| 2010/0074669 A1 | 3/2010 | Liu |
| 2010/0133172 A1 | 6/2010 | Song et al. |
| 2010/0155268 A1 | 6/2010 | Murray et al. |
| 2010/0200002 A1 | 8/2010 | Orban, III et al. |
| 2010/0240750 A1 | 9/2010 | Ash et al. |
| 2010/0256576 A1 | 10/2010 | Aggarwal et al. |
| 2010/0322996 A1 | 12/2010 | Wibaux et al. |
| 2011/0056852 A1 | 3/2011 | Frojd |
| 2011/0060317 A1 | 3/2011 | Frojd |
| 2011/0100526 A1 | 5/2011 | Umebayashi |
| 2011/0114520 A1 | 5/2011 | Matthison-Hansen |
| 2011/0118670 A1 | 5/2011 | Kay et al. |
| 2011/0137296 A1 | 6/2011 | Tanghoj |
| 2011/0152843 A1 | 6/2011 | Wedlin et al. |
| 2011/0178507 A1 | 7/2011 | Bracken et al. |
| 2011/0184386 A1 | 7/2011 | House |
| 2011/0213025 A1 | 9/2011 | Finch, Jr. |
| 2011/0284409 A1 | 11/2011 | Murray et al. |
| 2012/0029451 A1 | 2/2012 | Conway |
| 2012/0145589 A1 | 6/2012 | Macinnes et al. |
| 2012/0179144 A1 | 7/2012 | Carleo |
| 2012/0203182 A1 | 8/2012 | Kay et al. |
| 2012/0228165 A1 | 9/2012 | Murray et al. |
| 2012/0271101 A1 | 10/2012 | Tan |
| 2012/0316515 A1 | 12/2012 | Terry |
| 2013/0006226 A1 | 1/2013 | Hong et al. |
| 2013/0037306 A1 | 2/2013 | Kim |
| 2013/0112589 A1 | 5/2013 | Lien et al. |
| 2013/0131647 A1 | 5/2013 | Nielsen |
| 2013/0138083 A1 | 5/2013 | Tennican |
| 2013/0138088 A1 | 5/2013 | Nielsen |
| 2013/0153446 A1 | 6/2013 | Utas et al. |
| 2014/0142554 A1 | 5/2014 | Conway et al. |
| 2014/0142555 A1 | 5/2014 | Conway et al. |
| 2014/0262252 A1 | 9/2014 | Slepicka et al. |
| 2015/0025489 A1 | 1/2015 | Conway et al. |
| 2017/0021135 A1 | 1/2017 | Engelhardt |
| 2017/0216558 A1 | 8/2017 | Hughett et al. |
| 2017/0304590 A1 | 10/2017 | Conway et al. |
| 2018/0133434 A1 | 5/2018 | Conway et al. |
| 2020/0352775 A1 | 11/2020 | Brinkley |
| 2020/0398023 A1 | 12/2020 | Conway et al. |

FOREIGN PATENT DOCUMENTS

| | | |
|---|---|---|
| CN | 201248791 Y | 6/2009 |
| CN | 101896218 A | 11/2010 |
| CN | 202173496 U | 3/2012 |
| DE | 1913976 U | 4/1965 |
| DE | 19826746 C1 | 11/1999 |
| EP | 0055023 A2 | 6/1982 |
| EP | 0182409 A1 | 5/1986 |
| EP | 0184629 A2 | 6/1986 |
| EP | 0187846 A1 | 7/1986 |
| EP | 0193406 A2 | 9/1986 |
| EP | 0218203 A1 | 4/1987 |
| EP | 0236458 A1 | 9/1987 |
| EP | 0252918 A1 | 1/1988 |
| EP | 0298634 A1 | 1/1989 |
| EP | 0303487 A2 | 2/1989 |
| EP | 0335564 A1 | 10/1989 |
| EP | 0352043 A1 | 1/1990 |
| EP | 0390720 A1 | 10/1990 |
| EP | 0407218 A1 | 1/1991 |
| EP | 0217771 B1 | 12/1991 |
| EP | 0471553 A1 | 2/1992 |
| EP | 0479935 A1 | 4/1992 |
| EP | 0528965 A1 | 3/1993 |
| EP | 0553960 A1 | 8/1993 |
| EP | 0590104 A1 | 4/1994 |
| EP | 0598191 A1 | 5/1994 |
| EP | 0663196 A1 | 7/1995 |
| EP | 0677299 A1 | 10/1995 |
| EP | 0680895 A1 | 11/1995 |
| EP | 0685179 A1 | 12/1995 |
| EP | 0699086 A1 | 3/1996 |
| EP | 0767639 A1 | 4/1997 |
| EP | 0768069 A1 | 4/1997 |
| EP | 0815037 A1 | 1/1998 |
| EP | 0909249 A1 | 4/1999 |
| EP | 0923398 A1 | 6/1999 |
| EP | 0935478 A1 | 8/1999 |
| EP | 0972536 A1 | 1/2000 |
| EP | 0977610 A2 | 2/2000 |
| EP | 1023882 A1 | 8/2000 |
| EP | 1047360 A1 | 11/2000 |
| EP | 1115450 A1 | 7/2001 |
| EP | 1131022 A1 | 9/2001 |
| EP | 1245205 A2 | 10/2002 |
| EP | 0959930 B1 | 12/2002 |
| EP | 1308146 A1 | 5/2003 |
| EP | 1347723 A1 | 10/2003 |
| EP | 1406690 A2 | 4/2004 |
| EP | 1090656 B1 | 5/2004 |
| EP | 1427467 A2 | 6/2004 |
| EP | 1485158 A2 | 12/2004 |
| EP | 1498151 A2 | 1/2005 |
| EP | 1578308 A1 | 9/2005 |
| EP | 1145729 B1 | 11/2005 |
| EP | 1606196 A2 | 12/2005 |
| EP | 1615690 A1 | 1/2006 |
| EP | 1629799 A1 | 3/2006 |
| EP | 1641510 A1 | 4/2006 |
| EP | 1642610 | 4/2006 |
| EP | 1642611 | 4/2006 |
| EP | 1647298 A2 | 4/2006 |
| EP | 1786501 A2 | 5/2007 |
| EP | 1788990 A1 | 5/2007 |
| EP | 1793938 A1 | 6/2007 |
| EP | 1799163 A1 | 6/2007 |
| EP | 1904003 A2 | 4/2008 |
| EP | 1948279 A1 | 7/2008 |
| EP | 1955683 A1 | 8/2008 |

(56) References Cited

FOREIGN PATENT DOCUMENTS

| | | |
|---|---|---|
| EP | 2072075 A1 | 6/2009 |
| EP | 2216064 A1 | 8/2010 |
| EP | 2226041 A2 | 9/2010 |
| EP | 2226042 A2 | 9/2010 |
| EP | 2258435 A1 | 12/2010 |
| EP | 2275058 A1 | 1/2011 |
| EP | 2292293 A1 | 3/2011 |
| EP | 2292294 A1 | 3/2011 |
| EP | 2423125 A1 | 2/2012 |
| EP | 2423126 A1 | 2/2012 |
| EP | 2423127 A1 | 2/2012 |
| EP | 2450076 A1 | 5/2012 |
| EP | 2468347 A1 | 6/2012 |
| FR | 1558162 A | 2/1969 |
| FR | 2794638 A1 | 12/2000 |
| FR | 2855399 A1 | 12/2004 |
| GB | 322426 A | 12/1929 |
| GB | 1131865 A | 10/1968 |
| GB | 2150938 A | 7/1985 |
| GB | 2187670 A | 9/1987 |
| JP | 2010-533562 A | 10/2010 |
| JP | 2011-506009 A | 3/2011 |
| WO | 1984001102 A1 | 3/1984 |
| WO | 1986000816 A1 | 2/1986 |
| WO | 1986006284 A1 | 11/1986 |
| WO | 1987001582 A1 | 3/1987 |
| WO | 1989009626 A1 | 10/1989 |
| WO | 1990004431 A1 | 5/1990 |
| WO | 1991010466 A1 | 7/1991 |
| WO | 1991010467 A1 | 7/1991 |
| WO | 1991017728 A1 | 11/1991 |
| WO | 1992008426 A1 | 5/1992 |
| WO | 1992010220 A1 | 6/1992 |
| WO | 1992011826 A1 | 7/1992 |
| WO | 1992019192 A1 | 11/1992 |
| WO | 1993000054 A1 | 1/1993 |
| WO | 93/11821 A1 | 6/1993 |
| WO | 1993011821 A1 | 6/1993 |
| WO | 1993014806 A1 | 8/1993 |
| WO | 1994006377 A1 | 3/1994 |
| WO | 1994016747 A1 | 8/1994 |
| WO | 1994026215 A1 | 11/1994 |
| WO | 1995008968 A1 | 4/1995 |
| WO | 1995009667 A1 | 4/1995 |
| WO | 1995017862 A1 | 7/1995 |
| WO | 1995034253 A1 | 12/1995 |
| WO | 1996000541 A1 | 1/1996 |
| WO | 1996004119 A1 | 2/1996 |
| WO | 1996019254 A1 | 6/1996 |
| WO | 1996026688 A1 | 9/1996 |
| WO | 1996030277 A1 | 10/1996 |
| WO | 1996034587 A1 | 11/1996 |
| WO | 1996038192 A1 | 12/1996 |
| WO | 1996039096 A1 | 12/1996 |
| WO | 1997025947 A1 | 7/1997 |
| WO | 1997026937 A1 | 7/1997 |
| WO | 1997041811 A1 | 11/1997 |
| WO | 1998006642 A1 | 2/1998 |
| WO | 1999007313 A1 | 2/1999 |
| WO | 1999030761 A1 | 6/1999 |
| WO | 1999036009 A1 | 7/1999 |
| WO | 2000025848 A2 | 5/2000 |
| WO | 2000030575 A1 | 6/2000 |
| WO | 2000047494 A1 | 8/2000 |
| WO | 2001043807 A1 | 6/2001 |
| WO | 2001052763 A1 | 7/2001 |
| WO | 2001093935 A1 | 12/2001 |
| WO | 2002036192 A1 | 5/2002 |
| WO | 2002053070 A1 | 7/2002 |
| WO | 2002060361 A2 | 8/2002 |
| WO | 03/008028 A2 | 1/2003 |
| WO | 2003002178 A2 | 1/2003 |
| WO | 2003008029 A2 | 1/2003 |
| WO | 2003/022333 A1 | 3/2003 |
| WO | 2003064279 A1 | 8/2003 |
| WO | 2003092779 A1 | 11/2003 |
| WO | 2004004611 A1 | 1/2004 |
| WO | 2004004796 A1 | 1/2004 |
| WO | 2004030722 A2 | 4/2004 |
| WO | 2004032992 A2 | 4/2004 |
| WO | 2004045696 | 6/2004 |
| WO | 2004050155 A1 | 6/2004 |
| WO | 2004052440 A1 | 6/2004 |
| WO | 2004056290 A1 | 7/2004 |
| WO | 2004056414 A1 | 7/2004 |
| WO | 2004056909 A1 | 7/2004 |
| WO | 2004075944 A2 | 9/2004 |
| WO | 2004089454 A1 | 10/2004 |
| WO | 2005004964 A1 | 1/2005 |
| WO | 2005014055 A2 | 2/2005 |
| WO | 2005061035 A1 | 7/2005 |
| WO | 2005092418 A1 | 10/2005 |
| WO | 2006005349 A2 | 1/2006 |
| WO | 2006009509 A1 | 1/2006 |
| WO | 2006009596 A1 | 1/2006 |
| WO | 2006017439 A2 | 2/2006 |
| WO | 2006021590 A1 | 3/2006 |
| WO | 2006027349 A1 | 3/2006 |
| WO | 2006/086250 A2 | 8/2006 |
| WO | 2006097109 A2 | 9/2006 |
| WO | 2006110695 A2 | 10/2006 |
| WO | 2006112782 A1 | 10/2006 |
| WO | 2006130776 A2 | 12/2006 |
| WO | 2007001526 A2 | 1/2007 |
| WO | 2007038988 A1 | 4/2007 |
| WO | 2007083033 A2 | 7/2007 |
| WO | 2008089770 A1 | 7/2008 |
| WO | 2008104603 A1 | 9/2008 |
| WO | 2008138351 A1 | 11/2008 |
| WO | 2008138352 A1 | 11/2008 |
| WO | 2009000277 A1 | 12/2008 |
| WO | 2009012336 A1 | 1/2009 |
| WO | 2009043872 A1 | 4/2009 |
| WO | 2009068043 A2 | 6/2009 |
| WO | 2009080265 A1 | 7/2009 |
| WO | 2009108243 A1 | 9/2009 |
| WO | 2010006620 A1 | 1/2010 |
| WO | 2010054659 A1 | 5/2010 |
| WO | 2010054666 A1 | 5/2010 |
| WO | 2010129362 A1 | 11/2010 |
| WO | 2010130261 A1 | 11/2010 |
| WO | 2010149174 A1 | 12/2010 |
| WO | 2010149175 A1 | 12/2010 |
| WO | 2010151682 A2 | 12/2010 |
| WO | 2011011023 A1 | 1/2011 |
| WO | 2011014201 A1 | 2/2011 |
| WO | 2011019359 A1 | 2/2011 |
| WO | 2011026929 A1 | 3/2011 |
| WO | 2011026930 A1 | 3/2011 |
| WO | 2011063816 A1 | 6/2011 |
| WO | 2011073403 A1 | 6/2011 |
| WO | 2011076211 A1 | 6/2011 |
| WO | 2011079129 A1 | 6/2011 |
| WO | 2011109393 A1 | 9/2011 |
| WO | 2012016570 A2 | 2/2012 |
| WO | 2012016571 A2 | 2/2012 |
| WO | 2012018402 A1 | 2/2012 |
| WO | 2012079590 A1 | 6/2012 |
| WO | 2012134804 A1 | 10/2012 |
| WO | 2013010745 A1 | 1/2013 |
| WO | 2013029621 A1 | 3/2013 |
| WO | 2014081853 A1 | 5/2014 |
| WO | 2014081859 A1 | 5/2014 |

OTHER PUBLICATIONS

U.S. Appl. No. 13/705,695, filed Dec. 5, 2012 Non-Final Office Action dated Aug. 26, 2014.
U.S. Appl. No. 14/508,450, filed Oct. 7, 2014 Non-Final Office Action dated Jun. 29, 2015.
U.S. Appl. No. 15/649,296, filed Jul. 31, 2017 Non-Final Office Action dated Jul. 30, 2019.

(56) References Cited

OTHER PUBLICATIONS

U.S. Appl. No. 15/649,296, filed Jul. 31, 2017 Notice of Allowance dated Oct. 17, 2019.
U.S. Appl. No. 15/869,758, filed Jan. 12, 2018 Non-Final Office Action dated Mar. 23, 2020.
Vapro Product Brochure, 2009.
EP 12159487.3 filed Mar. 14, 2012 Communication under Rule 71(3) dated Apr. 28, 2020.
EP 13857538.6 filed Apr. 29, 2015 Communication pursuant to Article 94(3) dated Apr. 30, 2020.
PCT/US2018/051550 filed Sep. 18, 2018 International Preliminary report on Patentability dated Nov. 30, 2018.
PCT/US2018/051550 filed Sep. 18, 2018 International Search Report and Written Opinion dated Nov. 30, 2018.
U.S. Appl. No. 15/869,758, filed Jan. 12, 2018 Notice of Allowance dated May 29, 2020.
Amirkhalili, Saeid et al., "Mitric Oxide Complexes of Trimethylaluminium," Jornal of Organometallic Chemistry, 149 (Jan. 20, 1978) 407-411.
Angus Chemie GmbH Technical Data Sheet for AMP-95 dated Mar. 6, 2006.
CN 201380060729.1 filed May 20, 2015 Office Action dated Aug. 29, 2018.
CN 201380060729.1 filed May 20, 2015 Office Action dated Feb. 6, 2018.
CN 201380060729.1 filed May 20, 2015 Office Action dated Jul. 26, 2017.
CN 201380060729.1 filed May 20, 2015 Office Action dated Mar. 14, 2019.
CN 201380060729.1 filed May 20, 2015 Office Action dated Nov. 4, 2016.
CN 201380060741.2 filed May 20, 2015 First Office Action dated May 3, 2016.
CN 201380060741.2 filed May 20, 2015 Office Action dated Aug. 9, 2017.
CN 201380060741.2 filed May 20, 2015 Office Action dated Dec. 19, 2016.
CN201280065776.0 filed Jul. 1, 2014, First Office Action dated Jun. 4, 2015.
CN201280065776.0 filed Jul. 1, 2014, Second Office Action dated Jan. 20, 2016.
EP 12159487.3 filed Mar. 14, 2012 Exam Report dated Jul. 31, 2014.
EP 12159487.3 filed Mar. 14, 2012 Office Action dated May 22, 2018.
EP 12159487.3 filed Mar. 14, 2012 Office Action dated Oct. 12, 2015.
EP 12159487.3 filed Mar. 14, 2012 Third Party Observations dated Dec. 2, 2016.
EP 12159487.3 filed Mar. 14, 2012 Third Party Observations dated Sep. 8, 2015.
EP 13856790.4 filed Apr. 28, 2015 Extended European Search Report dated Jul. 1, 2016.
EP 13856790.4 filed Apr. 28, 2015 Office Action dated Jul. 2, 2019.
EP 13856790.4 filed Apr. 28, 2015 Office Action dated Oct. 19, 2018.
EP 13857538.6 filed Apr. 29, 2015 Extended European Search Report dated Jun. 17, 2016.
Ethomeen C/25 Information Sheet dated Jul. 28, 2005.
Johnson, James et al., "Activities of a Nitrofurazone-Containing Urinary Catheter and a Silver Hydrogel Catheter against Multidrug-Resistant Bacteria Characteristic of Catheter-Associated Urinary Tract Infection," Antimicrobial Agents and Chemotherapy, col. 43, No. 12, Dec. 1999, pp. 2990-2995.
JP 2015-543140 filed May 14, 2015 Notice of Allowance dated Feb. 22, 2018.
JP 2015-543140 filed May 14, 2015 Office Action dated Jul. 6, 2017.
JP 2015-543140 filed May 14, 2015 Office Action dated Oct. 18, 2017.
JP 2015-543141 filed May 19, 2015 Office Action dated Apr. 27, 2018.
JP 2015-543141 filed May 19, 2015 Office Action dated Aug. 10, 2017.
JP 2015-543141 filed May 19, 2015 Office Action dated Sep. 18, 2019.
Lubrizol Technical Data Sheet, Neutralizing Carbopol®* and Pemulen™ Polymers in Aqueous and Hydroalcoholic Systems, Sep. 16, 2009.
MX/a/2014/005144 filed Apr. 28, 2014 Office Action dated Jul. 14, 2016.
MX/a/2015/006058 filed May 13, 2015 Office Action dated May 25, 2018.
MX/a/2015/006059 filed May 13, 2015 Office Action dated Mar. 14, 2018.
Newman, Diane et al., "Review of Intermittent Catheterization and Current Best Practices," Urol Nurs. 2011:31(1).
PCT/US13/71046 filed Nov. 20, 2013 International Search Report and Written Opinion dated Feb. 21, 2014.
PCT/US13/71060 filed Nov. 20, 2013 International Search Report and Written Opinion dated Jan. 30, 2014.
PCT/US2012/068248 filed Dec. 6, 2012 International Preliminary Report on Patentability dated Jun. 10, 2014.
U.S. Appl. No. 11/104,388, filed Apr. 12, 2005 Notice of Allowance dated Mar. 21, 2014.
U.S. Appl. No. 13/047,175, filed Mar. 14, 2011 Decision on Appeal dated Feb. 28, 2017.
U.S. Appl. No. 13/047,175, filed Mar. 14, 2011 Examiner's Answer dated Nov. 4, 2014.
U.S. Appl. No. 13/047,175, filed Mar. 14, 2011 Final Office Action dated Mar. 17, 2014.
U.S. Appl. No. 13/682,406, filed Nov. 20, 2012 Decision on Appeal dated Jan. 29, 2018.
U.S. Appl. No. 13/682,406, filed Nov. 20, 2012 Examiner's Answer dated Aug. 11, 2016.
U.S. Appl. No. 13/682,406, filed Nov. 20, 2012 Final Office Action dated Jun. 5, 2015.
U.S. Appl. No. 13/682,406, filed Nov. 20, 2012 Non-Final Office Action dated Apr. 21, 2014.
U.S. Appl. No. 13/682,406, filed Nov. 20, 2012 Non-Final Office Action dated Nov. 28, 2014.
U.S. Appl. No. 13/682,420, filed Nov. 20, 2012 Decision on Appeal dated Jun. 16, 2017.
U.S. Appl. No. 13/682,420, filed Nov. 20, 2012 Examiner's Answer dated Apr. 8, 2015.
U.S. Appl. No. 13/682,420, filed Nov. 20, 2012 Final Office Action dated Jul. 15, 2014.
U.S. Appl. No. 13/682,420, filed Nov. 20, 2012 Non-Final Office Action dated Apr. 2, 2014.
U.S. Appl. No. 16/640,690, filed Feb. 20, 2020 Non-Final Office Action dated Nov. 18, 2021.
U.S. Appl. No. 16/640,690, filed Feb. 20, 2020 Advisory Action dated Jul. 6, 2022.
U.S. Appl. No. 16/640,690, filed Feb. 20, 2020 Final Office Action dated Apr. 28, 2022.
U.S. Appl. No. 16/640,690, filed Feb. 20, 2020 Notice of Allowance dated Aug. 26, 2022.

* cited by examiner

CATHETER GRIP AND METHOD

PRIORITY

This application is a continuation of U.S. patent application Ser. No. 15/649,296, filed Jul. 13, 2017, now U.S. Pat. No. 10,569,051, which is a continuation of U.S. patent application Ser. No. 13/047,175, filed Mar. 14, 2011, now U.S. Pat. No. 9,707,375, each of which is incorporated by reference in its entirety into this application.

FIELD OF THE INVENTION

The present invention includes an apparatus for gripping a catheter and methods employing it. The catheter grip can be configured to surround a shaft of a catheter and allow a person to manipulate the catheter without the person touching the insertable length of the catheter. The method includes grasping the gripping apparatus for removing the catheter from its package and for inserting the catheter into an urethra.

BACKGROUND OF THE INVENTION

A urinary catheter is an elongated tube that should remain sterile when removed from the package, that may be deployed in any of a variety of situations and environments, and that may be inserted by a lay person. In fact, the person inserting the catheter may have limited mobility or be handicapped. The person may be inserting the catheter in a public rest room. Therefore, there remains a need for devices and systems that aid in keeping a catheter clean as it is inserted and that assist a person in handling the catheter.

SUMMARY OF THE INVENTION

The present invention includes an apparatus for gripping a catheter and methods employing it. The catheter grip can be configured to surround a shaft of a catheter and allow a person to manipulate the catheter without the person touching the insertable length of the catheter. The method includes grasping the gripping apparatus for removing the catheter from its package and for inserting the catheter into an urethra.

In an embodiment, the present invention includes a catheter grip. The catheter grip can include a generally tubular body including a first end and a second end, defining a through bore, and configured to slidably engage the shaft of a urinary catheter. The generally tubular body can have a larger diameter at the first end and at the second end than at its middle.

In an embodiment, the present invention includes a system including a urinary catheter (e.g., a hydrophilic urinary catheter) and the present catheter grip.

In an embodiment, the present invention includes a method employing the present catheter grip. This method can include gripping a catheter grip on a shaft of a urinary catheter and positioned proximal an outlet end of the urinary catheter, removing the urinary catheter from a package, moving the catheter grip toward the insertable end of the urinary catheter, and holding the catheter grip and inserting the insertable end of the urinary catheter into a subject's urethra.

DETAILED DESCRIPTION

Figure 1:
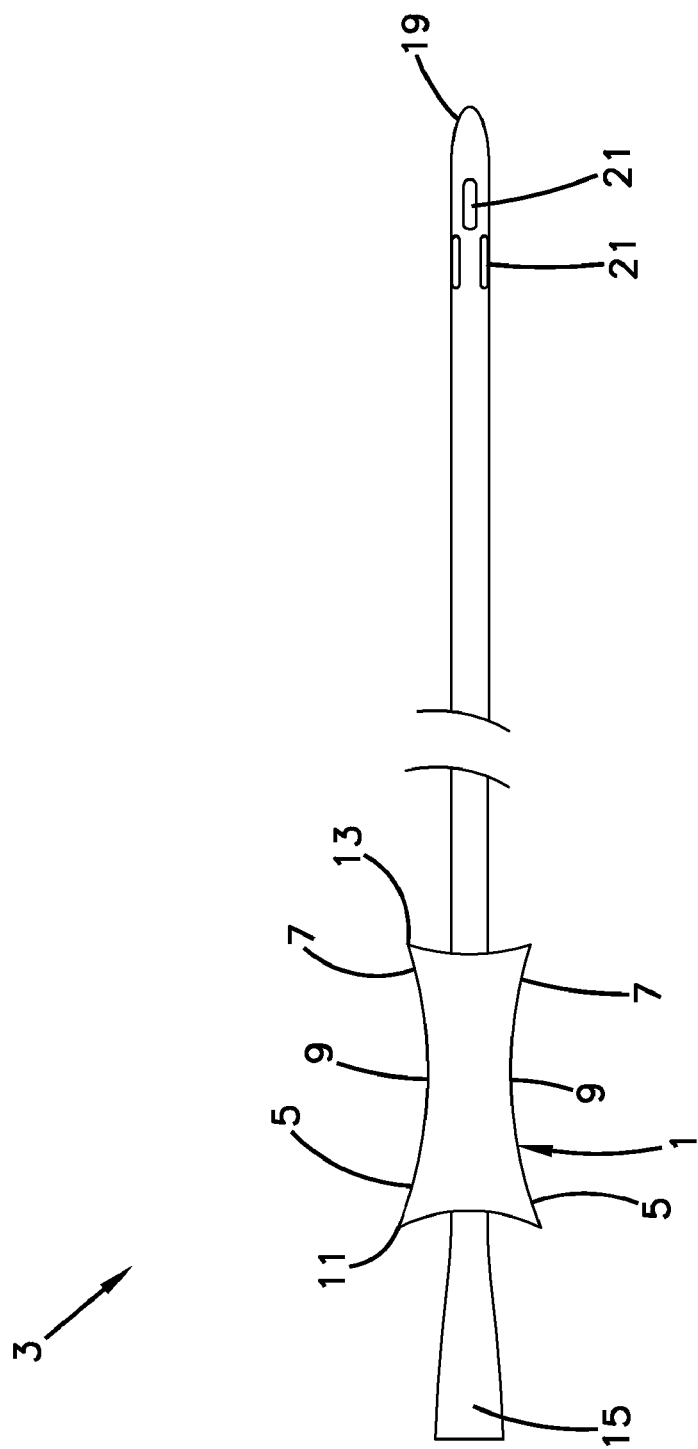
FIG. 1 schematically illustrates an embodiment of a urinary catheter and the catheter grip according to the present invention.

As used herein, the phrase "hydrophilic catheter" refers to a catheter on which the shaft and tip have a hydrophilic surface that when wet that provides advantageous lubrication during insertion and use of the hydrophilic catheter.

As used herein, the phrase "hydrophilic urinary catheter" refers to a hydrophilic catheter sized and constructed for occupying a mammalian urethra and draining a mammalian bladder.

As used herein, the phrase "insertable length" of a hydrophilic urinary catheter refers to the length of the catheter shaft that is coated with the hydrophilic material and inserted into the subject's urethra. For a human female subject, the insertable length is about 80-140 mm. For a human male subject, the insertable length is about 200-350 mm.

As used herein the phrase "generally tubular" refers to a configuration of the catheter grip that is capable of residing on and surrounding the shaft of a catheter, such as a urinary catheter. A generally tubular device can be tubular or cylindrical. A generally tubular device can have a cross section in the shape of any closed polygon, circle, or ellipse. For example, the generally tubular device can have a cross section in the shape of a triangle, square, pentagon, hexagon, octagon, or the like.

The present invention includes an apparatus for gripping a catheter, e.g., a hydrophilic urinary catheter, and methods employing this apparatus. The catheter grip is configured to surround a shaft of a catheter and allow a person to manipulate the catheter without the person touching the insertable length of the catheter. The shape of the catheter grip can be generally tubular (e.g., tubular), but smaller diameter in the middle and flared toward one or both ends. A configuration that is flared toward both ends can aid in positioning the user's fingers toward the middle of the catheter grip. The narrower middle portion of a configuration that is flared toward both ends provides a catheter contact area that is smaller than achieved by an unflared gripper. As a user applies force to the catheter grip, this smaller contact area directs that force to a smaller area of the catheter, which can provide a better grip. The flared configuration also distances the ends of the catheter grip from any coating that might be on the surface of a, for example, hydrophilic catheter and reduces the likelihood that the end of the grip can damage the coating.

The present catheter grip can be moved along the shaft of a catheter. For example, the catheter grip can be at the end of the catheter that is not inserted into a subject (the drainage end) for removing the catheter from its package. The catheter grip can be moved nearer the end of the catheter that is inserted into the subject (the insertable end) for insertion of the catheter. Such a catheter grip can slidably engage the shaft of the catheter.

The present method can include gripping the catheter grip to remove the catheter from the package, positioning the catheter grip near the insertable end of the catheter, and inserting the catheter into a subject's urethra. This method can also include moving the catheter toward the drainage end as the catheter is inserted into the subject's urethra. For removing the catheter from the package, the method can include positioning the catheter grip near the drainage end while the catheter is in the package. Thus, the catheter can be removed from the package and inserted into the subject's urethra without the user (e.g., the subject or a health care professional) touching the insertable length of the catheter directly (e.g., with their skin (fingers, hand, etc.).

The present method can include gripping the catheter grip to remove the catheter from the package, positioning the catheter grip near the insertable end of the catheter, and inserting the catheter into a subject's urethra and then optionally repositioning it toward the drainage end, re-gripping, and further inserting, and repeating this until insertion complete. It should be noted that this is the same motion of relaxing the fingers and repositioning as is done without the gripper.

In an embodiment, a flared gripper allows the user to deploy a catheter in the manner to which they are accustomed. For example, a user can grip the flared gripper between their thumb and forefinger. With a tight grip, the user can advance the catheter into the urethra. Yet, with a relaxed grip, the user does not release the doubly flared gripper. The double flare allows the fingers to remain in contact with the gripper even when relaxed from the tight grip. With the relaxed grip, the user can move their hand (and the gripper) back along the shaft of the catheter. Then, tightening the user's grip allows them to insert more of the catheter into the urethra. The user does not require new training or a new motion to deploy a catheter with a doubly flared gripper.

The outer surface of the catheter grip can be textured to facilitate, for example, gripping the catheter grip. The inner surface of the catheter grip can be textured to, for example, increase friction with the surface of the catheter when the compressive force is applied to the grip.

FIG. 1 schematically illustrates an embodiment of a urinary catheter and the catheter grip according to the present invention. The illustrated embodiment includes flared gripper 1 and catheter 3. Flared gripper 1 includes first flare 5, second flare 7, and mid-section 9. The diameter of flared gripper 1 at mid-section 9 is less than the diameter at either first flare 5 or second flare 7. The diameter at first end 11 and second end 13 can be equal, approximately equal, or different. In an embodiment, the diameter at first end 11 is equal (within manufacturing and design tolerances) to the diameter at second end 13.

Catheter 3 includes outlet 15, shaft 17, tip 19, and eyelet 21. Shaft 17 and tip 19 define a lumen (not shown) leading from eyelet 21 to outlet 15. Tip 19 and a major portion of shaft 17 of catheter 3 can be coated with an optional hydrophilic coating (not shown).

Figure 2:
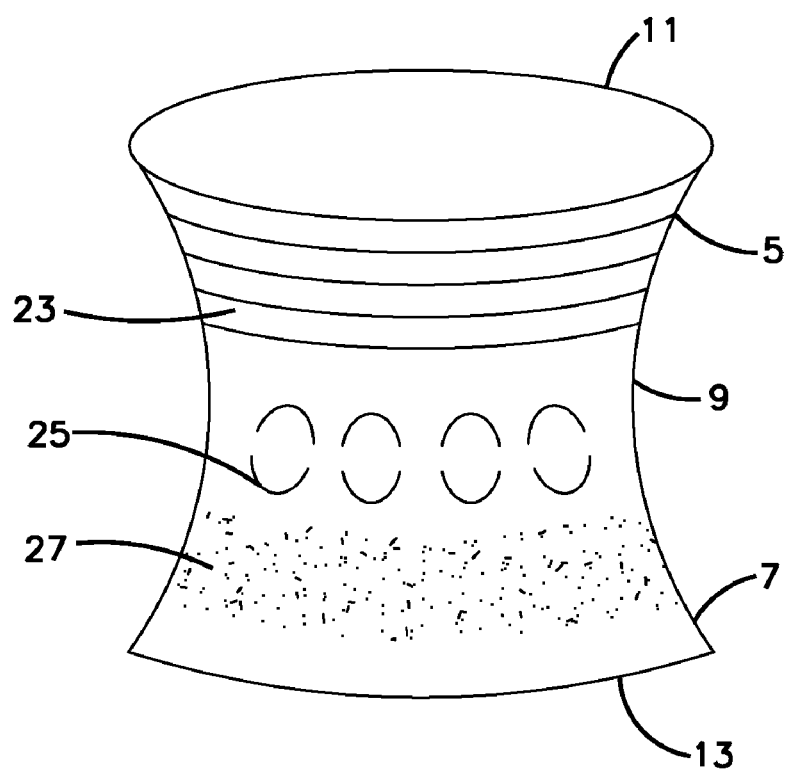
FIG. 2 schematically illustrates an embodiment of the catheter grip according to the present invention.

FIG. 2 schematically illustrates an embodiment of the catheter grip according to the present invention. As in FIG. 1, flared gripper 1 includes first flare 5, second flare 7, and mid-section 9. FIG. 2 also schematically illustrates optional textures of the exterior surface of flared gripper 1. These optional textures include raised ribs 23, pebbles 25, and roughening 27. Other suitable textures can also be employed. Such textures can also be employed on the inner surface of flared gripper 1 (not shown).

Figure 3:
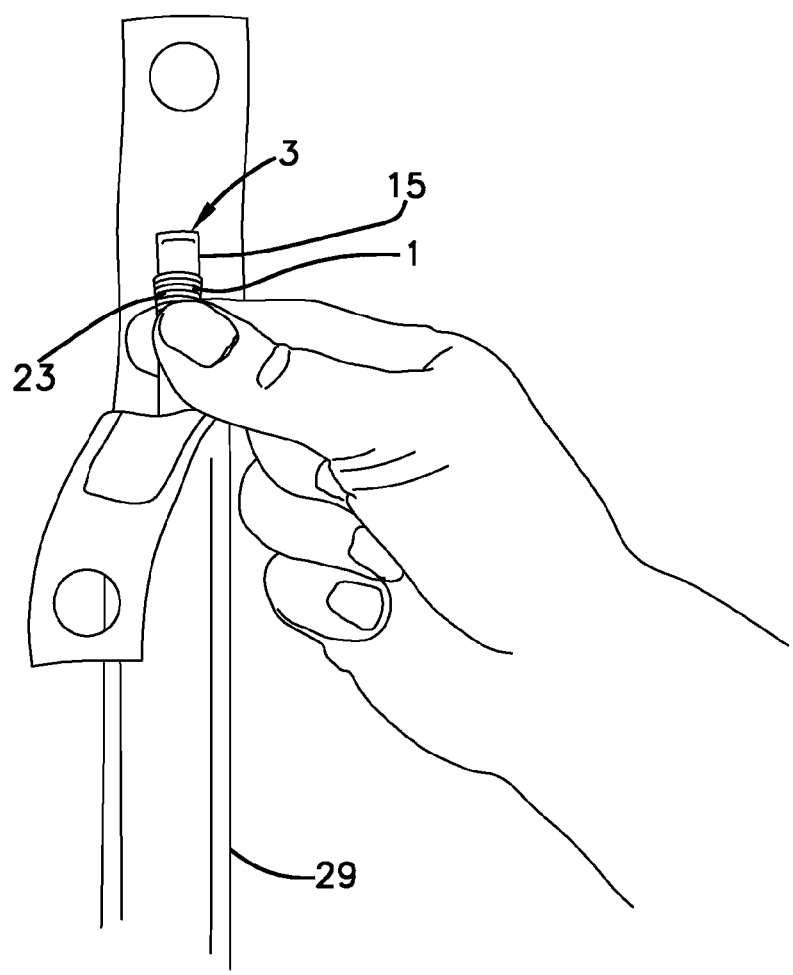
FIG. 3 schematically illustrates an embodiment of the catheter grip according to the present invention positioned near a drainage port of a urinary catheter in its packaging.

FIG. 3 schematically illustrates an embodiment of the flared gripper 1 positioned proximal the outlet 15 of catheter 3 in package 29. This embodiment of flared gripper 1 includes raised ribs 23. As shown in this Figure, a user can use thumb and forefinger to grip flared gripper 1. The user can then remove catheter 3 from the package 29.

Figure 4:
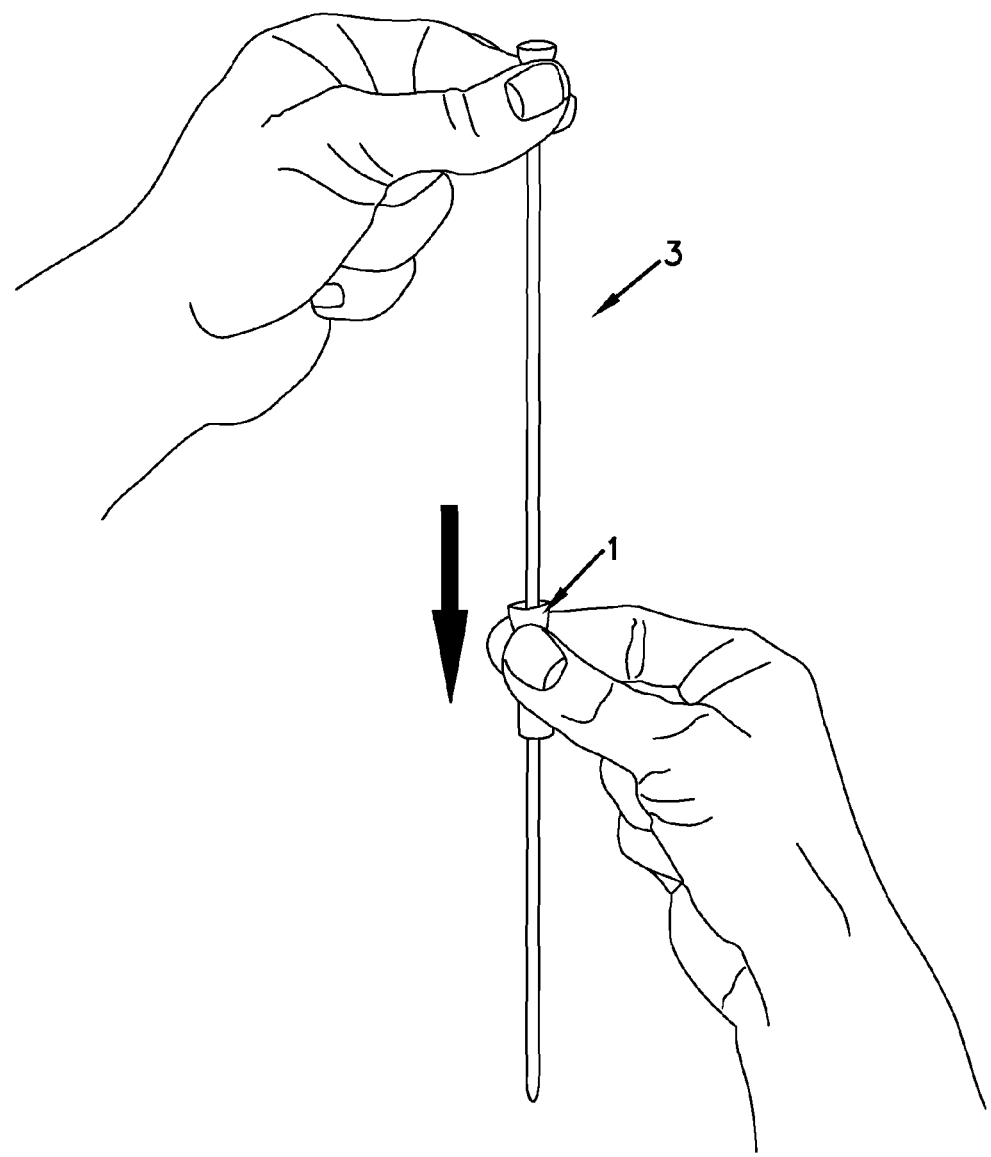
FIG. 4 schematically illustrates an embodiment of the catheter grip according to the present invention being moved along the shaft of a urinary catheter.

FIG. 4 schematically illustrates an embodiment of the flared gripper 1 being moved from proximal the outlet 15 of catheter 3 toward its tip 19. It can be easier for the user to control the location of the tip 19 when the flared gripper 1 is nearer the tip 19. The flared gripper 1 can be moved away from the tip 19 as the tip 19 is inserted into the urethra.

In an embodiment, the catheter grip includes a "double flare" shape that provides a "pinch point" in the middle. This pinch point is a much narrower contact area when the gripper is squeezed than a plain cylindrical or flat grip apparatus would provide. Thus, the squeeze force is directed to a smaller area, which provides a higher psi applied to the catheter grip, which in turn provides for a better grip.

The present invention includes an apparatus for gripping a catheter and methods employing it. The catheter grip can be configured to surround a shaft of a catheter and allow a person to manipulate the catheter without the person touching the insertable length of the catheter. The method includes grasping the gripping apparatus for removing the catheter from its package and for inserting the catheter into an urethra.

The present catheter grip can include a generally tubular body including a first end and a second end, defining a through bore, and configured to slidably engage the shaft of a urinary catheter. The generally tubular body can have a larger diameter at the first end and at the second end than at its middle. In addition, the catheter grip can also include texture on its surface(s). For example, the catheter grip can include an inner surface and an outer surface, each surface can include a texture selected from the group consisting of raised ribs, pebbling, roughening, or a combination thereof.

In an embodiment, the present invention includes a system including a urinary catheter (e.g., a hydrophilic urinary catheter) and the present catheter grip. The system can also include a package containing the urinary catheter and the catheter grip. The catheter grip can be disposed on a shaft of the urinary catheter. The system can include additional components also. For example, the system can include a packet of catheter wetting fluid, which can be contained in the package. In an embodiment, the system includes a prewetted hydrophilic catheter. In such an embodiment, the system typically does not include the packet of catheter wetting fluid.

Catheters suitable for the present system and method include catheters that benefit from wetting before use, for example, before insertion into a subject. Such a catheter is referred to herein as a wettable catheter. Wettable catheters include hydrophilic catheters, such as hydrophilic urinary catheters.

In an embodiment, the catheter package has a configuration of an elongated sheath, pouch, envelope, pocket, or the like. In an embodiment the catheter container, can be formed from material that provides a view of the catheter against an opaque or translucent background. For example, the catheter container can be formed from a sheet of transparent material and a sheet of opaque or translucent material. The sheets can be bonded together around the perimeter of a cavity containing the catheter and the fluid packet. For example, the catheter container can be in the form of a pouch formed from a translucent material and a clear material, a first side of the pouch comprising the translucent material and a second side of the pouch comprising the clear material. Such a pouch can be sealed around the edges. In an embodiment, the catheter is loose within the catheter container.

The present fluid packet can have a configuration and can be constructed of material suitable for containing fluid in a catheter container. The fluid packet can be configured for releasing fluid upon application of a force to the packet without opening the catheter container. For example, the fluid packet can include a fluid filled cavity bounded by two pieces of material bonded with a seam. Squeezing or striking such a fluid packet can breach the material or the seam and release the fluid. The material or seam can be substantially uniform around the edge.

The fluid packet can take any of a variety of forms, such as a sachet, an ampoule, a tube, or the like. The fluid packet can be made of any of a variety of materials such as aluminum foil, poly(vinylidene chloride), metallized film, or the like. The metallized film can be or include metallized poly(ethylene terephthalate). Preferably, the fluid packet is made from a hydrophobic material, such as a hydrophobic plastic, such as polyethylene or material including polyethylene. The fluid packet can include a first piece of packet material and a second piece of packet material. In this configuration, the first piece and second piece of packet material can be sealed to one another around the edges. The seal can be substantially uniform around the edge.

The fluid packet can contain any of a variety of fluids suitable for wetting a catheter. In an embodiment, the fluid is an aqueous wetting composition. The aqueous wetting composition can be any of a variety of aqueous wetting compositions suitable for wetting a catheter, such as a hydrophilic catheter. The aqueous wetting composition can be or include a sterile composition, such as sterile water (e.g. tap, deionized, or distilled water), sterile saline solution, or the like. In an embodiment, the aqueous wetting composition is or is made from distilled water. The fluid packet can contain a variety of antimicrobial agents in the aqueous wetting composition.

The present system can include any of a variety of components useful with the catheter. For example, the added component can be useful for using, removing, or disposing of the catheter. The present system can include a urine collection bag. The present system can include instructions about the use of the system or any part of the system. Such instructions, for example, can state that the catheter container be moved to move the wetting fluid over the insertable coated length of the catheter. Such instructions can be printed on the catheter container or on an instruction sheet included with the system. An article of manufacture can include the system plus one or more of these additional components.

In an embodiment, the present invention includes a method employing the present catheter grip. This method can include gripping a catheter grip on a shaft of a urinary catheter and positioned proximal an outlet end of the urinary catheter, removing the urinary catheter from a package, moving the catheter grip toward the insertable end of the urinary catheter, and holding the catheter grip and inserting the insertable end of the urinary catheter into a subject's urethra.

It should be noted that, as used in this specification and the appended claims, the singular forms "a," "an," and "the" include plural referents unless the content clearly dictates otherwise. Thus, for example, reference to a composition containing "a widget" includes a combination of two or more widgets. It should also be noted that the term "or" is generally employed in its sense including "and/or" unless the content clearly dictates otherwise.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

All publications and patent applications in this specification are indicative of the level of ordinary skill in the art to which this invention pertains The invention has been described with reference to various specific and preferred embodiments and techniques. However, it should be understood that many variations and modifications may be made while remaining within the spirit and scope of the invention.

What is claimed is:

1. A method for introducing a urinary catheter, comprising:
    obtaining a urinary catheter package, comprising:
        the urinary catheter; and
        a grip disposed over the urinary catheter, the grip comprising:
            a body designed to surround the urinary catheter, the body including a proximal end, a distal end, and a gripping area between the proximal end and the distal end, wherein the gripping area is designed to contact the urinary catheter upon application of force to the gripping area;
            a first flare increasing in cross-sectional area from the gripping area to the proximal end; and
            a second flare increasing in cross-sectional area from the gripping area to the distal end; and
    removing the urinary catheter from a proximal end of the urinary catheter package, the removing including holding the urinary catheter via the gripping area of the grip.

2. The method according to claim 1, wherein the body of the grip forms a curved outer surface from the proximal end of the body to the distal end of the body.

3. The method according to claim 1, wherein the grip further comprises a texture on at least one of an inner surface and an outer surface.

4. The method according to claim 3, wherein the texture is selected from the group consisting of raised ribs, pebbling, roughening, and a combination thereof.

5. The method according to claim 1, wherein the urinary catheter package further comprising a packet of catheter wetting fluid.

6. The method according to claim 5, wherein the urinary catheter is a hydrophilic urinary catheter, further comprising the step of releasing fluid in the urinary catheter package prior to removing the urinary catheter.

7. The method according to claim 1, wherein the urinary catheter package includes a closed cavity filled with a fluid, the closed cavity bonded with a seam, further comprising breaking the seam to release the fluid in the urinary catheter package to wet an outer hydrophilic surface of the urinary catheter.

8. The method according to claim 1, wherein the body is generally tubular, wherein the proximal end has a first diameter and the distal end has a second diameter, and wherein the first diameter is approximately the same as the second diameter.

9. The method according to claim 8, wherein at least one of the first diameter and the second diameter is a largest diameter of the grip.

10. The method according to claim 9, wherein the gripping area is located in a middle of the body.

11. The method according to claim 1, wherein the first flare and the second flare meet at the gripping area to provide a pinch point designed to contact the urinary catheter.

12. The method according to claim 1, wherein the removing step includes opening the urinary catheter package at the proximal end, and positioning the grip at an outlet end of the urinary catheter.

13. The method according to claim 12, further comprising sliding the grip toward an inlet end of the urinary catheter prior to introducing the urinary catheter.

14. The method according to claim 13, further comprising inserting the inlet end of the urinary catheter into a patient while sliding the grip toward the outlet end of the urinary catheter.

\* \* \* \* \*